(12) United States Patent
Jessen

(10) Patent No.: US 6,283,126 B1
(45) Date of Patent: Sep. 4, 2001

(54) HAND SHIELD

(76) Inventor: Bertha E. Jessen, 232 Fort Path Rd., Madison, CT (US) 06443

( * ) Notice: Subject to any disclaimer, the term of this patent is extended or adjusted under 35 U.S.C. 154(b) by 0 days.

(21) Appl. No.: 09/394,250

(22) Filed: Sep. 13, 1999

(51) Int. Cl.$^7$ ........................................... A61F 5/37
(52) U.S. Cl. ................................. 128/878; 128/879
(58) Field of Search .................... 128/845, 846, 128/877, 878, 879; 602/20, 21, 22

(56) References Cited

U.S. PATENT DOCUMENTS

| | | |
|---|---|---|
| 1,053,204 | 2/1913 | Morrison . |
| 2,043,153 * | 6/1936 | Cox ..................................... 128/879 |
| 2,139,897 | 12/1938 | Kessler . |
| 2,271,580 * | 2/1942 | Abell ................................... 128/879 |
| 3,182,657 | 5/1965 | Zurbachen . |
| 3,253,589 | 5/1966 | Shook . |
| 3,415,244 | 12/1968 | Block . |
| 3,416,518 * | 12/1968 | Samuels .................................. 602/3 |
| 3,471,207 | 10/1969 | Fuson . |
| 3,476,108 | 11/1969 | Matukas . |
| 4,893,372 | 1/1990 | Nenzel . |
| 4,982,745 * | 1/1991 | Shields ................................ 128/877 |
| 5,063,919 | 11/1991 | Silverberg . |
| 5,279,574 | 1/1994 | Forren . |
| 5,761,746 | 9/1998 | Brown . |

* cited by examiner

Primary Examiner—Michael A. Brown
(74) Attorney, Agent, or Firm—Robert H. Montgomery

(57) ABSTRACT

A hand shield for a patient comprising an element of flexible but stiff material adapted to be rolled into an open ended generally fustro-conical shape The element has a wrist wrap at the smaller end thereof. Cooperative releasable fastening means are disposed along the edges of the element and arranged to hold said element in said generally fustro-conical shape. Means are provided for fastening the wrist wrap about the wrist of a patient. An aperture is defined in the element intermediate the ends and sides thereof to permit passage of one or more needles there through to the back of a hand of a patient. The element is sufficiently long so as to extend beyond the fingers of the patient to prevent the fingers from grasping an object beyond the opening.

10 Claims, 2 Drawing Sheets

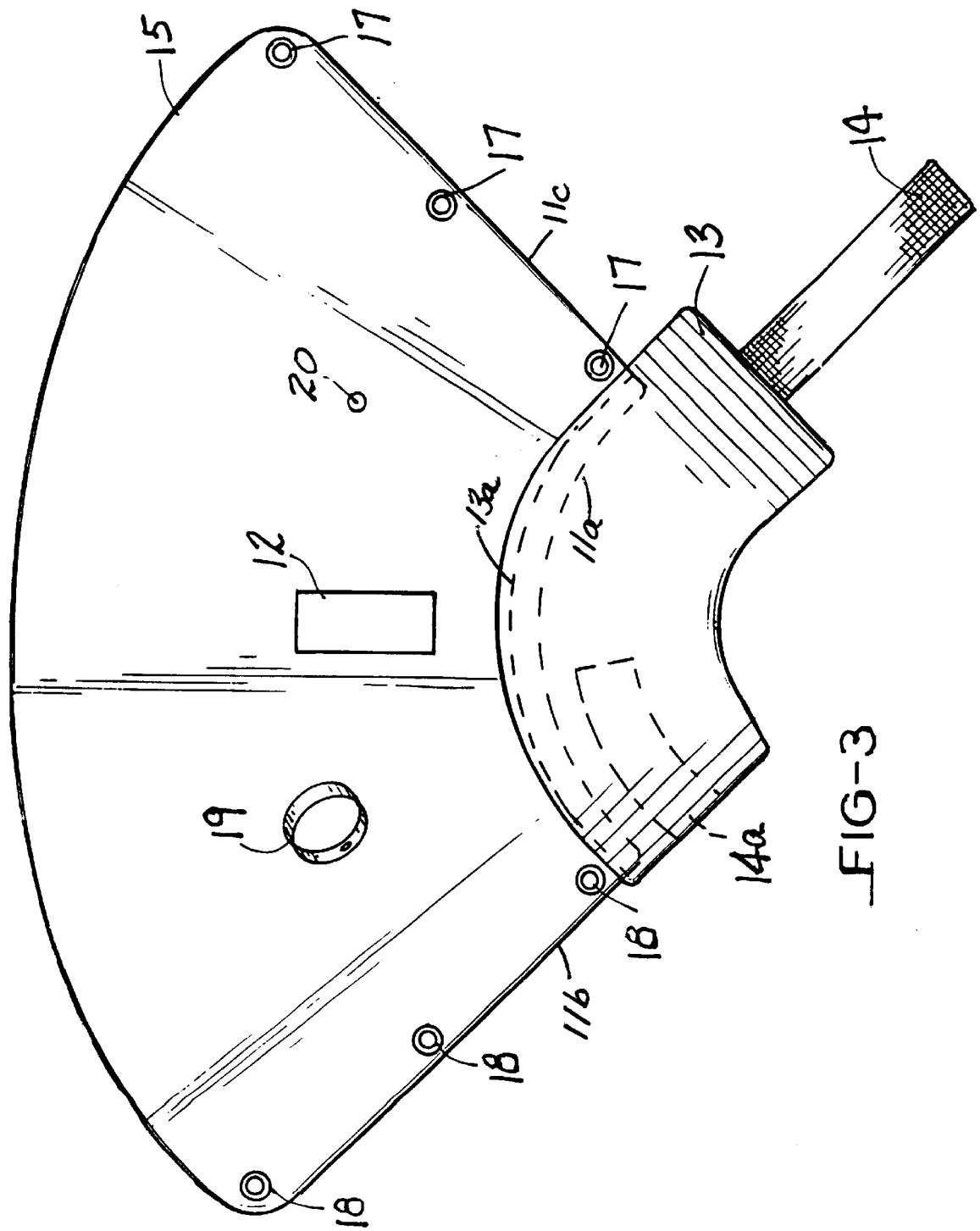

HAND SHIELD

FIELD OF THE INVENTION

This invention relates to hand shields of the type worn by a patient to prevent unintended removal of needles or catheters from the patient, scratching of wounds or removal of bandages

BACKGROUND OF THE INVENTION

Many bed patients are not alert and do not have full command of their facilities due to a variety of causes including among others process of recovery from anesthesia, trauma, sedation, age etc. Such patients often involuntarily attempt to remove bandages, scratch wounds remove catheters or intravenous needles or make other detrimental use of their hands.

Various hand shields or guards have been proposed to prevent one or more of these activities. For the most part known hand shields for bed patients attempt to immobile the hands and fingers and completely enclose the hand and only permit limited, if any, air circulation over the skin. This leads to detrimental skin conditions. With patients prone to perspiration constant moisture on the hands leads to maceration of the skin. In some other patients the lack of air circulation over the skin cause dryness, cracking, scaling and eventual peeling of the skin.

Accordingly the present invention provides a new and improve patient hand shield very simplified construction which prevents involuntary scratching, removal of bandages and removal of inserted catheters and needles.

The present invention provides a hand shield which is light in weight and does not interfere with normal movement of fingers within the shield yet prevents use of the hands and fingers to scratch, remove bandages or inserted catheters and needles. A hand shield embodying the invention is not restrictive to the patient and permits the grasping and squeezing of objects within the shield, such as a rubber ball, to exercise the hand An object of this invention is to provide a new and improved hand shield for a bed patient to prevent involuntary removal of bandages, scratching of wounds or sores and removal of catheters and tubes such as gastric and nasal.

A further object of this invention is to provide such a hand shield which does not prevent air circulation over and around a patient's hands.

A further object of this invention is to provide a such new and improved hand shield which is light in weight which permits patients to normally move their fingers but prevents use of the hand fingers for detrimental purposes.

SUMMARY OF THE INVENTION

Briefly stated, the invention, comprises a hand shield for a bed patient which is frustro-conical in shape with the smaller end secured about a patient's wrist. The larger end is open and extends beyond the fingers of the patient. The large open end permits air to circulate about the patient's hand and fingers and thus protects the skin from any adverse effects of lack of circulation. A hand shield embodying the invention, in one form thereof, comprises an element of flexible but stiff material of generally modified trapezoidal shape adapted to be rolled into an open ended fustro-conical configuration. The element of modified trapezoidal shape has bases formed on radii, and has wrist wrap at the smaller base thereof. Cooperative releasable fastening means along the edges of the element arranged to hold the element in the generally fustro-conical shape when it is to be used. A strap is provided for fastening the wrist wrap about the wrist of a patient, and an aperture is defined in the element intermediate the ends and sides thereof and positioned to permit access therethrough to the back of a hand of a patient.

The features of the invention which are believed to be novel are particularly pointed out and distinctly claimed in the concluding portion of this specification. The invention, however, together with further objects and advantages thereof, may best be appreciated by reference to the following detailed description taken in conjunction with the drawings.

BRIEF DESCRIPTION OF THE DRAWINGS

FIG. 3 is a view seen in the plane if lines 3—3 of FIG. 2; and

DETAILED DESCRIPTION OF PREFERRED EMBODIMENT OF THE INVENTION

Figures 1, 4:
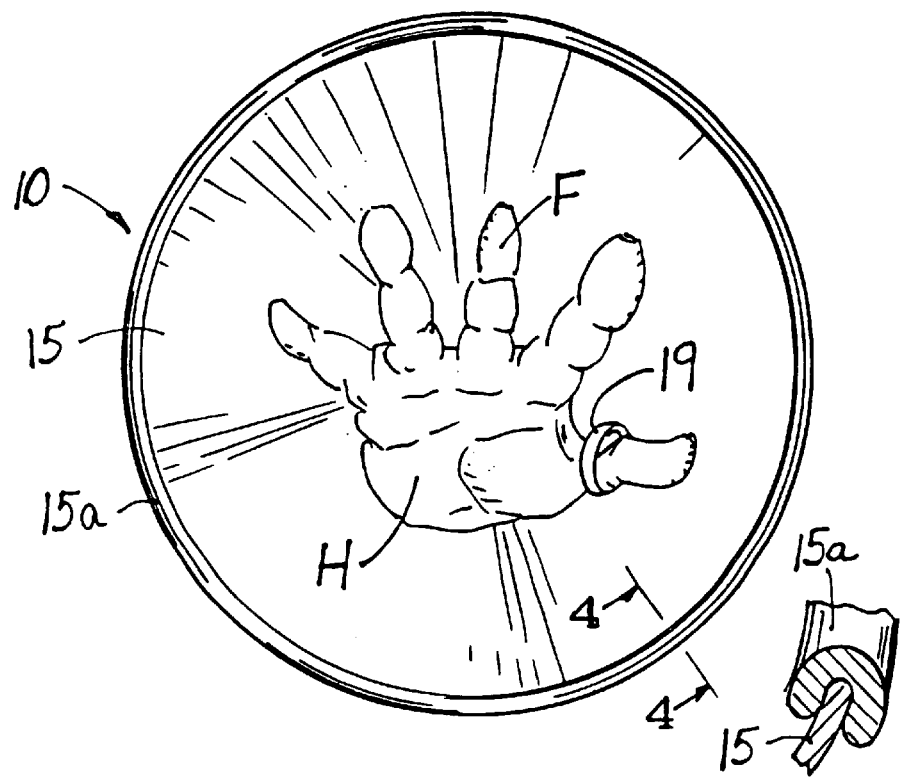
FIG. 1 is an end view of a device embodying the invention shown applied to a persons hand.
FIG. 4 is a plan view of the device of FIGS. 1 and 2, shown removed from the patient.
Figure 2:
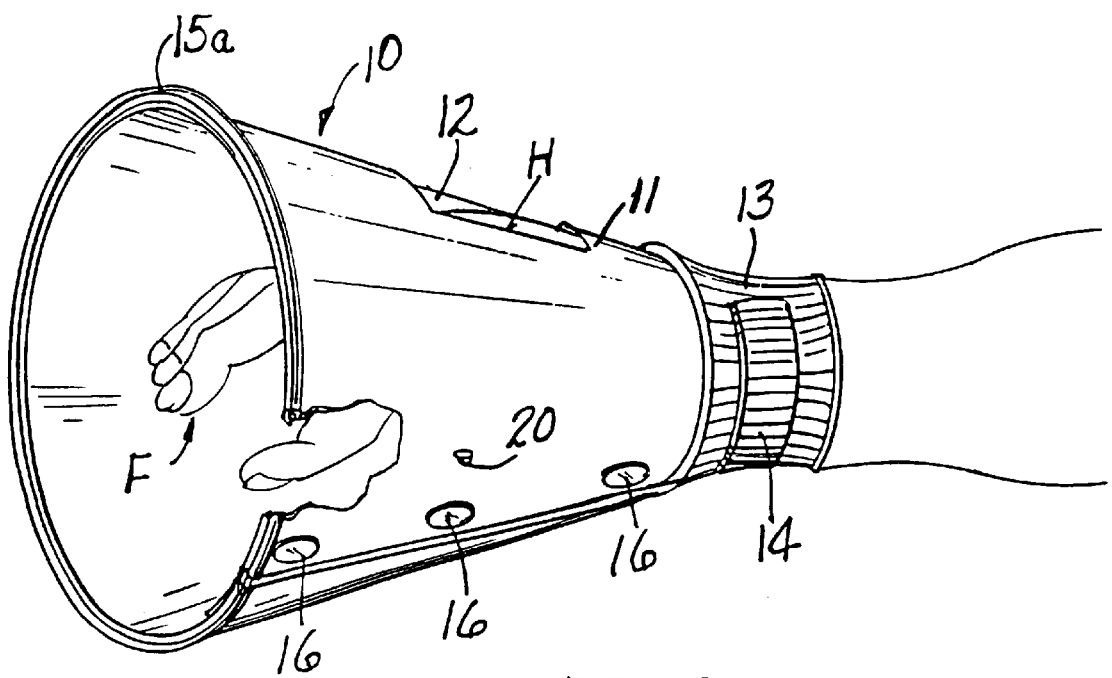
FIG. 2 is a side view shown in perspective of the device of FIG. 1.

Reference is now made to FIGS. 1 and 2. A hand shield 10 is shown disposed about the wrist of a patient and extending over a hand H and beyond the fingers F. The hand shield comprises a frustro-conical (in operative configuration) member 11 having an opening 12 defined therein over the back of hand H. A wrist band or wrap 13 is secured to the small inner end of member 11 as by stitching or any other suitable means as hereinafter described. Wrist wrap 13, in one acceptable form is made of an expandable or stretchable ribbing material of natural or synthetic fiber or a combination of both which will absorb any moisture due to sweating.

Member 11 terminates in an outer or distal base edge 15 which may receive a protective bead 15a thereon for reasons hereinafter explained. Base edge 15 defines the outer opening of the hand shield as seen in FIGS. 1 and 2.

Reference is now made to FIG. 3 taken in conjunction with FIGS. 1 and 2. Member 11 is of a generally modified trapezoidal shape. The shape is referred to as "modified" because the normal bases of a trapezoid are defined on radii. Outer edge 15 and inner edge 11a, FIG. 3, are formed on radii with the radius of outer edge 15 being substantially larger. Edges 11a and 15 are the bases of the generally modified trapezoid. Base edges 11a and 15 are joined by opposed side edges 11b and 11c to define element 11. Wrist wrap 13 is joined to element 11 adjacent base edge 11a as by stitching, represented by the broken line 13a. Member 11 is arranged to be rolled into a frustro-conical shape as shown in FIG. 2 and has means for fastening the side edges shown in the form of snaps 16, FIG. 2, which comprise male members 17 at one side adapted to be received in female 18 receptacles on the other side. Alternatively, hook and pile strips may be secured to the joined sides of member 11 adjacent the edges thereof to secure the sides together. One such hook and pile material is commonly known by the trademark Velcro.

The member 11 is formed, preferably of a plastic material which is sufficiently flexible enough to be rolled into the shape shown in FIG. 2, but sufficiently rigid when so rolled as not to be deformed or collapse. A suitable material is sheet polyvinyl chloride (PVC) of about 0.010 inch thickness or greater. If a softer material such as polypropylene is used the thickness will be increased to provide the stated desired characteristics of flexibility and rigidity. The material of member 11 may be transparent or opaque and may be colored.

Attached to the inside of member 11, as shown in FIG. 3, is a thumb loop 19 adapted to receive a thumb. Loop 19 is attached to member 11 by means of a snap 19a. This is designed to prevent the wrist wrap and hand shield 10 from longitudinal movement with respect to the arm. The loop 19 may be fastened to member 11 by a snap and an additional snap 20 is provided for such snap for either right hand or left hand use. Alternatively, two loops 19 may be provided so that one hand shield is suitable for use on either the right or left hand.

A hand shield embodying the invention may be made in different sizes for use with patients of different size hands. The different sizes of the hand shield will have members of different length so that the edge 15 extends at least one inch beyond out stretched fingers of the patient. This will prevent the patient from using his or her fingers to grasp and pull out any nasal, gastric, intravenous and other tubes. The member 11 is so sized that the edge 15 defining the opening is of sufficient size to permit air circulation about the hand and fingers, but not large enough to permit the patient to grasp a nasal or gastric tube by placing the open end defined by edge 15 over the chin. Usually, the opening defined by edge 15 will be about seven inches in diameter for an adult. This may vary with the size of the patients hands as may the length.

The wrist wrap has a strap 14 attached thereto and extending therefrom which has one of a hook and pile material on the side shown in FIG. 3. Positioned on the side opposite that shown in FIG. 3 is a strip or length of the other of the hook and pile material to mate with strap 14.

The hand shield is placed on a patient by positioning wrist wrap 13 around a patient's wrist, while placing the patient's thumb in loop 19 and then forming member 11 into a frustro-conical shape and securing snaps 16 or any other fastening means which may be used. Strap 14 is then secured to strip 14a to the desired degree of tightness. The hand shield is initially positioned so that the opening 12 exposes a portion of the back of the hand to permit insertion of catheters, needles or other skin piercing or intravenous devices. The steps of application of the hand shield stated above may be varied in order at the discretion of the person applying the hand shield to a patient.

The bead 15a is optionally provided to present a soft surface so that the end of member will not scratch or otherwise irritate any portion of the patient's body it may contact. The bead 15a also prevents the patient from irritating a wound by scratching.

It may be seen that with the hand shield 10 applied as shown in FIG. 2, the hand shield is open to at end 15 to permit free air circulation over the entire hand. If the patients hands are prone to perspiration this will aid in evaporation and prevent maceration. The air circulation will also combat drying, scaling, cracking and ultimate peeling of skin.

With the edge 15 extending beyond the fingers and the material of member 11 being rigid when in the operative position shown in FIG. 2, member 11 will not fold or collapse if rubbed against the skin. Finger or thumb hook 19 will prevent the patient from forcing the hand shield up the arm. A hand shield embodying the invention is very light in weight and will not be a burden to the patient.

It may thus be seen that the objects of the invention set forth above as well as those made apparent are efficiently attained. While a preferred embodiment of the invention has been set forth for purposes of disclosure, modifications to the disclosed embodiments as well as other embodiments of the invention may occur to those skilled in the art. Accordingly, the appended claims are intended to cover all modifications to the disclosed embodiments of the invention as well as other embodiments thereof which do not depart from the spirit and scope of the invention.

What is claimed is:

1. A hand shield for a patient comprising an element of flexible, but stiff, material of generally trapezoidal shape adapted to be formed into a frustro-conical configuration open at both ends, said element having large and small base edges formed on radii and opposed side edges joining said base edges, said element having a wrist wrap adjacent said smaller base edge thereof, cooperative releasable fastening means along the side edges of said element arranged to hold said element in said generally frustro-conical shape with said larger base edge defining an opening into the interior of said element, means for fastening said wrist wrap about the wrist of a patient, said element being of sufficient length to extend a distance beyond the fingers of a patient so as to prevent use of the fingers to grasp an object beyond said opening of said element and an aperture defined in said element intermediate the base edges and side edges thereof and positioned to permit passage of one or more needles therethrough to the back of a hand of a patient.

2. The shield of claim 1 further including means on said element arranged to engage a patient's finger to limit movement of said shield with respect to a patient's arm.

3. The hand shield of claim 2 wherein said means on said element arranged to be engaged with a patient's finger is a loop within said element when formed into a frustro-conical shape.

4. The hand shield of claim 1 further including a soft bead disposed along said larger base edge defining said open end.

5. A hand shield for a patient comprising a sheet of flexible, but stiff, material adapted to be rolled into a generally frustro-conical shape, said element having long and short end edges, said long end edge defining an opening at the larger end thereof when said element is rolled into said generally frustro-conical shape, said short end edge defining a smaller opening when said element is rolled into said generally frustro-conical shape and having means for attaching said element about the wrist of a patient at the smaller opening thereof, said element having spaced apart side edges joining said end edges, cooperative releasable fastening means disposed along said side edges and arranged to hold said element in said generally frustro-conical shape, said element being sufficiently long to extend beyond the fingers of the patient to prevent the fingers from grasping an object beyond said larger open end.

6. The shield of claim 5 including means on said element engagable with a patient's finger to limit movement of said shield with respect to a patient's arm.

7. The hand shield of claim 6 further wherein said means on said element arranged to engage a patient's finger to limit movement of said shield with respect to a patients arm is a loop.

8. The hand shield of claim 5 further including a soft bead disposed along said edge defining said larger open end.

9. The hand shield of claim 5 wherein an aperture is defined in said element and positioned intermediate end edges and said edges to permit access to the back of the hand of the patient for insertion of one or more needles into the hand of a patient.

10. The hand shield of claim 8 wherein said element is of modified trapezoidal shape with said end edges defined on radii.

\* \* \* \* \*